(12) United States Patent
Thiruvengadam et al.

(10) Patent No.: US 7,553,987 B2
(45) Date of Patent: Jun. 30, 2009

(54) SYNTHESIS OF 3-(5-NITROCYCLOHEX-1-ENYL) ACRYLIC ACID AND ESTERS THEREOF

(75) Inventors: Tiruvettipuram K. Thiruvengadam, Kendall Park, NJ (US); Tao Wang, Springfield, NJ (US); John S. Chiu, Parsippany, NJ (US); Jing Liao, Livingston, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/824,246

(22) Filed: Jun. 29, 2007

(65) Prior Publication Data

US 2008/0009651 A1 Jan. 10, 2008

Related U.S. Application Data

(60) Provisional application No. 60/817,866, filed on Jun. 30, 2006.

(51) Int. Cl.
C07C 205/00 (2006.01)
C07C 61/08 (2006.01)

(52) U.S. Cl. ...................... 560/125; 562/507
(58) Field of Classification Search ........................ None
See application file for complete search history.

(56) References Cited

U.S. PATENT DOCUMENTS 6,063,847 A 5/2000 Chackalamannil

FOREIGN PATENT DOCUMENTS

JP 2003-277329 * 10/2003

OTHER PUBLICATIONS

International Search Report for International Application No. PCT/US2007/015152 filed Jun. 29, 2007; mail date Jan. 11, 2008; 2 pages; published as WO2008/005344 on Apr. 3, 2008 with Search Report.
Aubry, J-M, et al.; " Preparative oxidation of Organic Compounds in Microemulsions with Singlet Oxygen Generated Chemically by the Sodium Molybdate/Hydrogen Peroxide System", J. Am. Chem. Soc.; 119(23); pp. 5286-5294; Jun. 1997.
Ballistreri, F. P., et al.; "Useful Oxidation Procedure of Oximes to Nitro Compounds with Benz-Mo in Acetonitrile", SYNLETT, pp. 1093 - 1094; Nov. 1996.
Bernaowicz, et. al.; "Development of Potent Thrombin Receptor Antagonist Peptides"; J. Med. Chem., 39, pp. 4879-4887; Jun. 1996.
Bortolini, O., et al.; "Metal Catalysis in Oxidation by Peroxides . . . ", J. Org. Chem., 52 (24); pp. 5467 - 5469; 1987.
Bose and Vanajatha; "A Versatile method for the conversion of oximes to nitroalkanes"; Synthetic Communications; 28 (24); pp. 4531-4535 (1998).
Chackalamannil, S., et. al., A Highly Efficient Total Synthesis of (+)-Himbacine. J. Am. Chem. Soc.; 118, pp. 9812 - 9813 (1996).
Emmons and Pagano, "Peroxytrifluoroacetic Acid. VI. The Oxidation of Oximes to Nitroparaffins", J. Am. Chem. Soc.; 77, pp. 4557 - 4559 (1955).
Iffland and Yen; "Preparation of Nitro Compounds from Oximes. III. The Synthesis of Nitroalkanes"; J. Am. Chem. Soc.; 76, pp. 4083 - 4085 (1954).
Iffland, et. al.; "The Preparation of Nitro Compounds from Oximes", J. Am. Chem. Soc.; 75: pp. 4044-4046; 4047 - 4048 (1954).
Nardello, V., et. al.; "Reactivity, chemoselectivity, and Diastereoselectivity . . . "; J. Am. Chem. Soc.; 126 (34); pp. 10692 - 10700 (2004).
Olah, et. al.; "Convenient Oxidation of Oximes to Nicto Compounds with Sodium Perborate in Glacial Acetic Acid", SYNLETT; pp. 337 - 339; Apr. 1992.
Tamami and Yeganeh; "Polymer supported anionic peroxomolymdenum complexes as new, mild, efficient and versatile oxidants in organic synthesis", Eur. Polym. J.; 35, pp. 1445 - 1450 (1999).

* cited by examiner

*Primary Examiner*—Paul A Zucker
(74) *Attorney, Agent, or Firm*—Patent Practitioners of Schering Corporation

(57) ABSTRACT

This application discloses provides a process for the introduction of nitro-group functionality into a compound which contains also a site of unsaturation and/or oxygen functionality by direct (one step) oxidation of an oxime functional group mediated by a molybdenum VI/VII peroxo complex, the process comprising:

(a) providing a substrate of Formula I containing an oxime functional group;

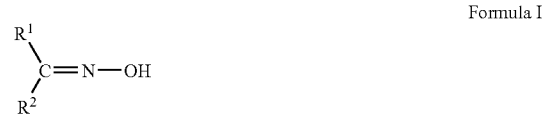

Formula I wherein $R^1$ and $R^2$ are selected independently from linear, branched or cyclic alkyl and linear, branched or cyclic alkenyl groups, optionally substituted, with the proviso that at least one of $R^1$ or $R^2$ contains a carbon/carbon double bond; and (b) contacting said substrate of Formula I with a molybdenum oxidation complex, thereby oxidizing said oxime functional group to a nitro functional group to yield the structure of Formula III.

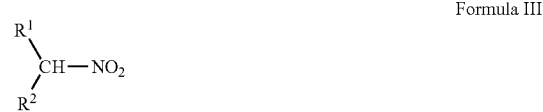

Formula III

Where $R^1$ and $R^2$ are as defined above.

22 Claims, No Drawings

US 7,553,987 B2

SYNTHESIS OF 3-(5-NITROCYCLOHEX-1-ENYL) ACRYLIC ACID AND ESTERS THEREOF

CROSS-REFERENCE TO RELATED APPLICATIONS

This application is based on and claims the priority of U.S. Provisional Application No. 60/817,866 filed Jun. 30, 2006, which is incorporated by reference herein in its entirety.

FIELD OF THE INVENTION

This application relates to a novel process for the preparation of nitro-substituted compounds via oxidation of oximes mediated by a peroxo molybdenum oxidation complex. More specifically, this invention provides for preparation of nitro-substituted compounds containing unsaturated functionality via direct oxidation of the corresponding oxime.

BACKGROUND OF THE INVENTION

Thrombin is known to have a variety of activities in different cell types and thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonists peptides have been identified based on structure-activity studies involving substitutions of amino acids on thrombin receptors. In Bernatowicz et al., *J. Med. Chem.*, 39, p. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor anatgonists are also disclosed in WO 94/03479, published Feb. 17, 1994.

Himbacine, a piperidine alkaloid, has been identified as a muscarinic receptor antagonist. The total synthesis of (+)-himbacine is disclosed in Chackalamannil et al., *J. Am. Chem Soc.*, 118, p. 9812-9813 (1996).

Thrombin receptor antagonists are known in the art. Examples of such compounds are disclosed in U.S. Pat. No. 6,063,847, herein incorporated by reference, Thrombin receptor antagonists are useful in the treatment of thrombotic, inflammatory, atherosclerotic and fibroproliferative disorders, as well as other disorders in which thrombin and its receptor play a pathological role.

Various process are described in the art to prepare himbacine analagoues. In addition to those disclosed in U.S. Pat. No. 6,063,847, other copending applications that describe processes to prepare himbacine analogues include U.S. patent application Ser. Nos. 11/331,324, 11/330,935, 11/330,936, and 11/330,521, all four applications filed on Jan. 12, 2006, and herein incorporated by reference. As illustrated below in Scheme VII, one of the processes disclosed in those applications employs the compound 3-(5-nitrocyclohex-1-enyl) acrylic acid (6) an intermediate in a process for the preparation of an orally bioavailable thrombin receptor antagonist (11). Each of copending U.S. patent application Ser. No. 11/331,324, (the '324 application) and Ser. No. 11/330,936 (the '936 application) also disclose processes utilizing 3-(5-nitrocyclohex-1-enyl) acrylic acid as an intermediate in the preparation of himbacine analogs. An example of one preparatory scheme is Scheme VII, below, described in the '324 application, which utilizes the acid (compound 6 in Scheme VII) in the provision of himbacine analog compound 11.

Scheme VII- the nitro-oxazole route for preparation of Compound 11:

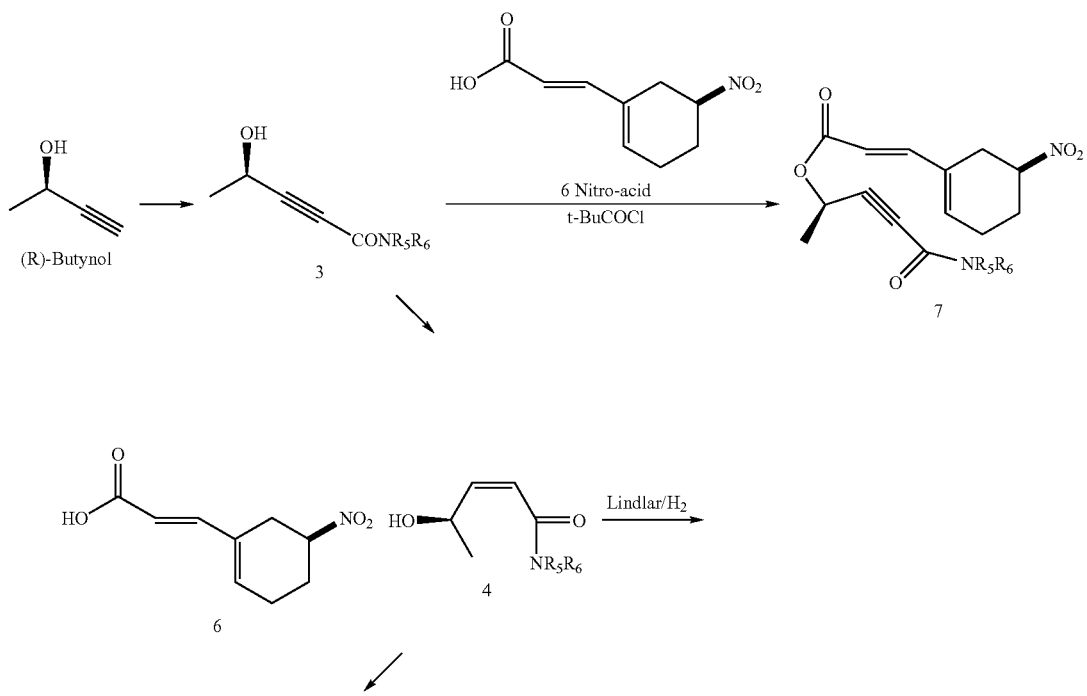

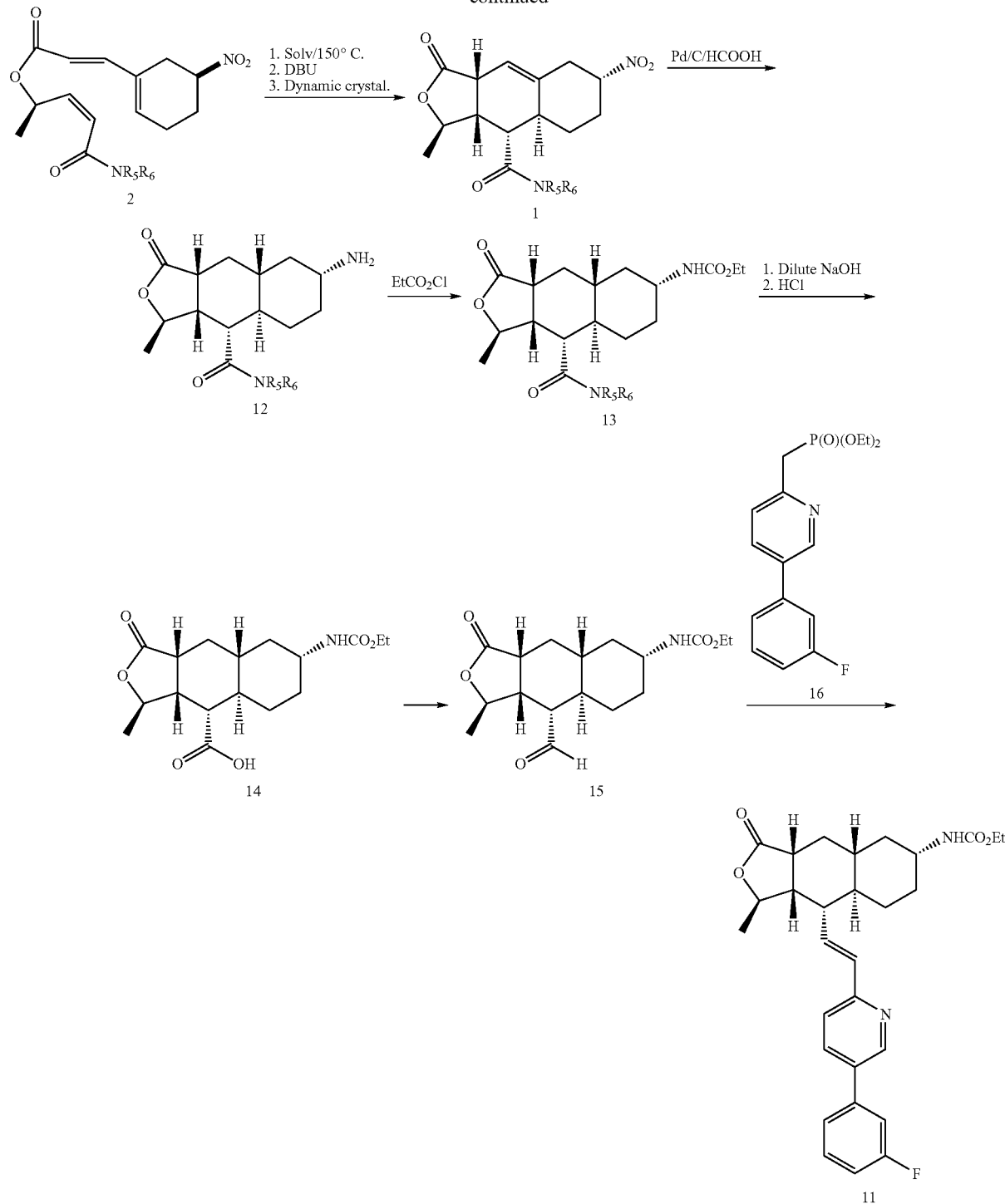

The '324 and '936 applications describe the preparation of 3-(5-nitrocyclohex-1-enyl) acrylic acid from acrolein and nitromethane, which is incorporated by reference herein. However the processes described entail many process steps and provide the acid in low yield and low purity, requiring additional steps to provide suitably pure material.

One possible approach to improved preparation of the acid intermediate is the isolation of the oxime analog of 3-(5-nitrocyclohex-1-enyl) acrylic acid (the compound of Formula IA, illustrated herein below) with subsequent oxidation of the oxime functional group to a nitro functional group.

Various reactions are known in the art to oxidize oximes to the corresponding nitro compound. For example, Olah, et al. in *SYNLETT*, pp 337-39 (April 1992) describe using sodium perborate in glacial acetic acid to form nitro compounds from the corresponding oxime. Emmons and Pagano, *J. Am. Chem.*

*Soc.,* 77, 4557-59 (1955), use peroxytrifluoroacetic acid as an oxidizing agent. Bose and Vanajatha use OXONE (potassium peroxymonosulfate) in acetonitrile to oxidize oximes to nitroalkanes (*Synth. Commun.*, 28, 4531-4535 (1998)). Iffland and Yen in *J. Am. Chem. Soc.,* 76, 4083-85 (1954) disclose using N-bromo-acetamide and zinc oxide to prepare nitroalkanes from the corresponding oxime. Other methods disclosed by Iffland are described in *J. Am. Chem. Soc.,* 75, 4044-46 and 4047-4048 (1954) and *J. Am. Chem. Soc.,* 75, 4083-85 (1954). Each of these oxidation processes are carried out using reagents and conditions which would oxidize other oxidation-sensitive groups present in the oxime, for example, unsaturated bonds, for example, carbon-carbon double bonds and carbon-carbon triple bonds. Accordingly, these methods would be unsuited to the provision of, for example, 3-(5-nitrocyclohex-1-enyl) acrylic acid by oxidation of the corresponding oxime.

Anionic molybdenum-peroxo complexes are known in the art to be effective oxidants for primary and secondary alcohols in nonpolar solvents. Bortolini et al., *J. Org. Chem.,* 52, 5467-69 (1987). Ballistreri et al. in *SYNLETT* pp. 1093-4 (November 1996) describe the oxidation of alkyl oximes to the corresponding nitroalkanes by employing an Mo(VI) oxodiperoxo complex catalyst in acetonitrile, however, none of the compounds disclosed therein contained reactive functional groups other than the oxime substituent.

Tamami and Yeganeh in *Eur. Polym. J.* 35,1445-1450 (1999), describe two polymer supported anionic peroxomolybdenuym compound that can be used as oxidizing agents for a variety of organic compounds including oximes, however, they report that these reagents produce the corresponding aldehyde from the oxime.

OBJECTIVES OF THE INVENTION

In view of the foregoing, there remains a need for new methods of synthesizing nitro-containing compounds directly from oximes containing other reactive functional groups. Further, there remains a need for an efficient process of oxidizing an oxime to a nitro functional group that is sufficiently selective such that to at least a substantial degree double bond(s) present also in the substrate moiety are not oxidized or isomerized in the process. Moreover, pertinent to the synthesis of compounds useful as thrombin receptor antagonists, as well as the synthesis of intermediates used to prepare these compounds, there is a need to develop efficient and selective methods for oxidizing oxime functional groups present in substrates containing double bonds and additional oxidation sensitive functional groups.

In view of the importance of thrombin receptor antagonists, new, novel methods of preparing intermediates for the provision of such antagonists are always of interest.

SUMMARY OF THE INVENTION

These and other advantages are met by the present invention.

In one embodiment the present invention provides a process for the introduction of nitro-group functionality into a compound which contains also a site of unsaturation and/or oxygen functionality by direct (one step) oxidation of an oxime functional group mediated by a molybdenum VI/VII peroxo complex, the process comprising:

(a) providing a substrate of Formula I containing an oxime functional group;

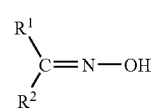

Formula I wherein $R^1$ and $R^2$ are selected independently from linear, branched or cyclic alkyl and linear, branched or cyclic alkenyl groups, optionally substituted with carboxylic, ester, halo, phenyl, cyano, alkyl, alkenyl aryl, cycloalkyl, cyano, alkoxy, alkylthio, —N(alkyl)$_2$, —N(cycloalkyl)$_2$, -carboxy and —C(O)O-alkyl functionality, or $R^1$ and $R^2$ are taken together to form a cycloalkenyl substitutent which is optionally substituted with one or more groups selected from linear, branched or cyclic alkyl and linear, branched or cyclic alkenyl functional groups, each of which may optionally be substituted with alkenyl, -carboxy, ester, halo, phenyl, cyano, alkyl, aryl, cycloalkyl, cyano, alkoxy, alkylthio, —N(alkyl)$_2$, and —N(cycloalkyl)$_2$, functional groups, with the proviso that at least one of $R^1$ or $R^2$ contains a carbon/carbon double bond; and (b) contacting said substrate of Formula I with a molybdenum oxidation complex, thereby oxidizing said oxime functional group to a nitro functional group to yield the structure of Formula III.

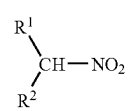

Formula III

Where $R^1$ and $R^2$ are as defined above.

In some embodiments of the inventive process the molybdenum oxidation complex used in step "b" is a molybdenum oxidation complex of Formula II,

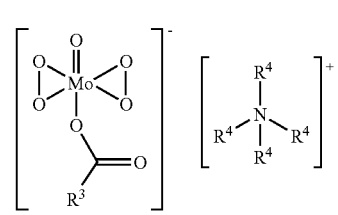

Formula II wherein $R^3$ is a benzyl group or an aryl group, each of which is optionally substituted with alkyl substituents and $R^4$ is selected from linear, branched, or cyclic alkyl of up to 12 carbon atoms. When the molybdenum oxidation complex of Formula II is used it is preferred to add at least one equivalent of the complex based on the amount of substrate to be oxidized. For most applications it is more preferably to use an amount of the complex of Formula II in excess of one equivalent, based on the amount of substrate to be oxidized. When a molybdenum oxidation complex of Formula II is used it is preferred to carry out the reaction in a polar, aprotic solvent, more preferably a solvent selected from acetone, and acetonitrile. Preferably the reaction is carried out at a temperature of from about 0° C. to about 100° C.

In some embodiments of the process of the invention, the molybdenum oxidation complex is prepared by separate or simultaneous addition to the reaction medium of sodium molybdate and peroxide ( referred to herein sometimes for convenience as "NaMolyOx"). When the molybdenum oxidation complex used is NaMolyOx, it is preferred to use an amount of sodium molybdate based on the number of moles of substrate to be oxidized equal to from about 0.1 equivalents to about 2.0 equivalents of sodium molybdate, more preferably from about 0.5 equivalents to about 1.5 equivalents of sodium molybdate, and more preferably 1.0 equivalents of sodium molybdate. In the same manner when NaMolyOx complex is used, it is preferred to use an amount of peroxide based on the number of moles of substrate to be oxidized equal to from about 1.0 equivalents to about 3.0 equivalents of peroxide, more preferably from about 1.2 equivalents to about 2.0 equivalents of peroxide, and more preferably 1.5 equivalents of peroxide. When an NaMolyOx complex is used it is preferred to carry out the reaction in a solvent comprising water miscible solvents, for example, acetonitrile (ACN), acetone, and dimethylformamide (DMF). Preferably the reaction is carried out at a temperature of from about 0° C. to about 100° C., more preferably at a temperature of from about 40° C. to about 60° C.

In some embodiments, the compound of the Formula I has the structure of the compound of Formula IA:

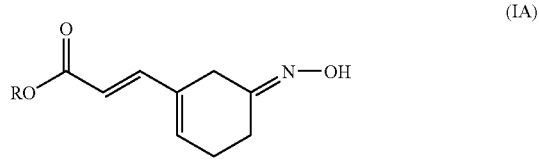

(IA)

wherein R is H, linear, branched or cyclic alkyl, optionally substituted, and linear branched or cyclic alkenyl, optionally substituted, wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocycloalkyl, each of which is optionally substituted.

thus, after treatment with the molybdenum oxidation complex, providing a compound having the structure of Formula III A

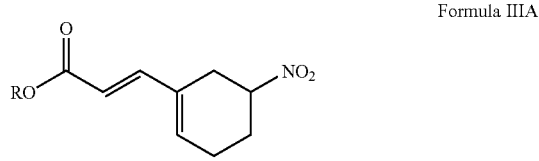

Formula IIIA where "R" is as defined above.

In some preferred embodiments the oxime of Formula IA is prepared by the process comprising:

(a) providing a protected ketal compound of the structure of Formula IV

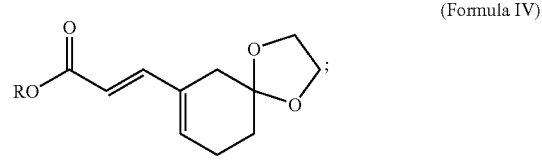

(Formula IV)

(b) hydrolyzing the compound of Formula IV, thus removing the ketal protecting group from the compound of formula IV to form a compound of the Formula V

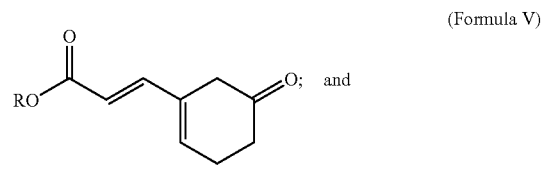

(Formula V)

and (c) contacting the compound of Formula V with hydroxylamine, thus converting the compound of Formula V to an oxime of the structure of Formula IA:

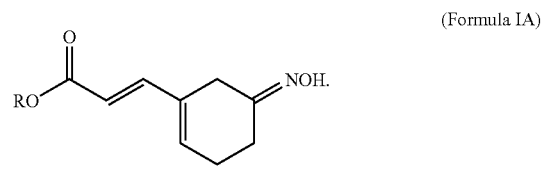

(Formula IA)

In some embodiments of the present invention utilizing this process for the provision of oxime to be oxidized, conversion step "c" is carried out without isolating the ketone prepared in step "b", by adding hydroxylamine in situ to a solution of the ketone formed in step "b". In some embodiments of the present invention utilizing this process for the provision of the oxime to be oxidized, the ketone is isolated after performing hydrolysis step "b" and the oxime formation step "c" is performed separated in time and/or space from the hydrolysis.

In some embodiments of the present invention, the compound of Formula I has the structure of the compound of Formula IB:

(Formula IB)

wherein "R" is as defined above and oxidation of the oxime by the present process provides a compound of the structure of Formula IB':

(Formula IB')

When oxime compounds of the structure of Formula IB are used it is preferred to carry out the oxidation reaction using a molybdenum oxidation complex provided by sodium molybdate and peroxide (NaMolyOx).

DESCRIPTION OF THE INVENTION

As used above, and throughout the specification, the following terms, unless otherwise indicated, shall be understood to have the following meanings:

"Nitro-containing compound means any organic compound that contains at least one nitro functional group (i.e., —$NO_2$ group).

"Oxime" means any organic compound that contains at least one oxime functional group (i.e., —C=N—OH group); see e.g., Wikipedia, http://en.wilkipedia.org/wilki/oxime, herein incorporated by reference.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl. The term "substituted alkenyl" means that the alkenyl group may be substituted by one or more substituents which may be the same or different, each substituent being independently selected from the group consisting of alkyl, aryl and cycloalkyl carboxylic, ester, halo, phenyl, cyano, alkyl, alkenyl aryl, cycloalkyl, cyano, alkoxy, alkylthio, —N(alkyl)$_2$, —N(cycloalkyl)$_2$, -carboxy and —C(O)O-alkyl functionality, "Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Cycloalkylether" means a non-aromatic ring of 3 to 7 members comprising an oxygen atom and 2 to 6 carbon atoms. Ring carbon atoms can be substituted, provided that substituents adjacent to the ring oxygen do not include halo or substituents joined to the ring through an oxygen, nitrogen or sulfur atom.

"Cycloalkenyl" means a non-aromatic mono or multicyclic ring system comprising about 3 to about 10 carbon atoms, preferably about 5 to about 10 carbon atoms which contains at least one carbon-carbon double bond. The cycloalkenyl ring can be optionally substituted with one or more ring system substituents which may be the same or different, and are as defined above. Preferred cycloalkenyl rings contain about 5 to about 7 ring atoms. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Aralkyl" or "arylalkyl" means an aryl-alkyl-group in which the aryl and alkyl are as previously described, including the optional substituents. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described, including the optional substituents. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Arylcycloalkyl" means a group derived from a fused aryl and cycloalkyl as defined herein. Preferred arylcycloalkyls are those wherein aryl is phenyl and cycloalkyl consists of about 5 to about 6 ring atoms. The arylcycloalkyl can be optionally substituted by one or more "ring system substituents". Non-limiting examples of suitable arylcycloalkyls include indanyl and 1,2,3,4-tetrahydronaphthyl and the like. The bond to the parent moiety is through a non-aromatic carbon atom.

"Arylheterocycloalkyl" means a group derived from a fused aryl and heterocycloalkyl as defined herein. Preferred arylcycloalkyls are those wherein aryl is phenyl and heterocycloalkyl consists of about 5 to about 6 ring atoms. The arylheterocycloalkyl can be optionally substituted by one or more "ring system substituents". Non-limiting examples of suitable arylheterocycloalkyls include

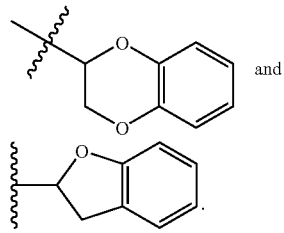

and

The bond to the parent moiety is through a non-aromatic carbon atom.

"Alkoxy" means an alkyl-O— group in which the alkyl group is as previously described including the optional subsitutents. Non-limiting examples of suitable alkoxy groups include methoxy, ethoxy, n-propoxy, isopropoxy, n-butoxy and heptoxy. The bond to the parent moiety is through the ether oxygen.

"Alkyoxyalkyl" means a group derived from an alkoxy and alkyl as defined herein, including the optional substituents. The bond to the parent moiety is through the alkyl.

"Arylalkenyl" means a group derived from an aryl and alkenyl as defined herein, including the optional substituents. Preferred arylalkenyls are those wherein aryl is phenyl and the alkenyl consists of about 3 to about 6 atoms. The bond to the parent moiety is through a non-aromatic carbon atom.

"Arylalkynyl" means a group derived from a aryl and alkenyl as defined herei, including the optional substituents. Preferred arylalkynyls are those wherein aryl is phenyl and the alkynyl consists of about 3 to about 6 atoms. The bond to the parent moiety is through a non-aromatic carbon atom.

The suffix "ene" on alkyl, aryl, hetercycloalkyl, etc. indicates a divalent moiety, e.g., —CH$_2$CH$_2$— is ethylene, and

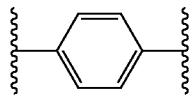

is para-phenylene.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, Y$_1$Y$_2$N—, Y$_1$Y$_2$N-alkyl-, Y$_1$Y$_2$NC(O)— and Y$_1$Y$_2$NSO$_2$—, wherein Y$_1$ and Y$_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in heterocyclyl ring systems of this invention, there are no hydroxyl groups on carbon atoms adjacent to a N, O or S, as well as there are no N or S groups on carbon adjacent to another heteroatom. Thus, for example, in the ring:

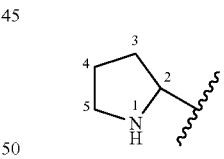

there is no —OH attached directly to carbons marked 2 and 5.

"Alkynylalkyl" means an alkynyl-alkyl-group in which the alkynyl and alkyl are as previously described including the optional substituents. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described including the optional substituents. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described including the optional subsitutents. Preferred heterocyclylalkyls contain a lower alkyl group, Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a nonaromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Hydroxyalkyl" means a HO-alkyl-group in which alkyl is as previously defined including the optional substituents. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described including the optional subsitutents. The bond to the parent moiety is through the carbonyl. Non-limiting examples of suitable groups include benzoyl and 1-naphthoyl.

"Alkoxy" means an alkyl-O— group in which the alkyl group is as previously described including the optional substituents. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described including the optional substituents. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described including the optional substituents. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described including the optional substituents. Non-limiting examples of suitable alkylthio groups include methylthio and ethylthio. The bond to the parent moiety is through the sulfur.

"Arylthio" means an aryl-S— group in which the aryl group is as previously described including the optional substituents. Non-limiting examples of suitable arylthio groups include phenylthio and naphthylthio. The bond to the parent moiety is through the sulfur.

"Aralkylthio" means an aralkyl-S— group in which the aralkyl group is as previously described including the optional substituents. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

Similarly, "heteroarylalkyl" "cycloalkylalkyl" and "heterocycloalkylalkyl" mean a heteroaryl-, cycloalkyl- or heterocycloalkyl-alkyl-group in which the heteroaryl, cycloalkyl, heterocycloalkyl and alkyl are as previously described. It is also understood that the terms "arylcycloalkylalkyl", "heteroarylcycloalkylalkyl", "arylheterocycloalkylalkyl", "heteroarylheterocycloalkylalkyl", "heteroarylcycloalkyl", "heteroarylheterocycloalkyl", "arylcycloalkenyl", "heteroarylcycloalkenyl", "heterocycloalkenyl", "arylheterocycloalkenyl", "heteroarylheterocycloalkenyl", "cycloalkylaryl", "heterocycloalkytaryl", "heterocycloalkenylaryl", "heterocycloalkylheteroaryl", "cycloalkenylaryl" and "heterocycloalkenylaryl" similarly represented by the combination of the groups aryl-, cycloalkyl-, alkyl-, heteroaryl-, heterocycloalkyl-, cycloalkenyl- and heterocycloalkenyl- as previously described, including the optional substituents. Preferred groups contain a lower alkyl group. The bond to the parent moiety is through the alkyl.

The term "optionally substituted" means optional substitution with the specified groups, radicals or moieties, in available position or positions.

Substitution on a cycloalkylalkyl, heterocycloalkylalkyl, arylalkyl, or heteroarylalkyl moiety includes substitution on the ring portion and/or on the alkyl portion of the group.

When a variable appears more than once in a group or a variable appears more than once in the structure the variables can be the same or different.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any heteroatom with unsatisfied valences in the text, schemes, and examples herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable occurs more than one time in any constituent or formula, its definition on each occurrence is independent of its definition at every other occurrence.

The term "salt(s)", as employed herein, denotes acidic salts formed with inorganic and/or organic acids, as well as basic salts formed with inorganic and/or organic bases. In addition, if a compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of a compound may be formed, for example, by reacting a compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, 35S, $^{18}F$, and $^{36}Cl$, respectively.

Isotopically labeled compounds can generally be prepared by following procedures analogous to those known in the art by substituting an appropriate isotopically labeled reagent for a non-isotopically labeled reagent.

The inventors have surprisingly discovered that oxime functional groups in compounds containing oxidation sensitive functionality, for example, ketone functional groups, aldehyde functional groups, ester functional groups, and double bonds, including double bonds conjugated with other functional groups having double bond character, for example, ketones and esters, can be oxidized to provide a nitro functional group, by direct oxidation without significant oxidation occurring at the sites of the other oxidation sensitive functionality present in the substrate, and without double bond rearrangement. Surprisingly, such oxidations can be mediated by molybdenum oxidation complexes described herein. Accordingly, the present invention is a process for providing nitro group functionality in a substrate bearing both an oxime and additional oxygen sensitive functional groups. Moreover, since ketone functional groups can be selectively converted to oxime functional groups, it is a process for the provision of introducing a nitro functional group into a substrate which contains a ketone functional group along with other oxidation sensitive functionality.

In addition, the present invention is a process for the provision of nitro compounds of the structure of Formula IIIA, which are critical intermediates in the provision of Thrombin Receptor Antagonists, for example, compound 6 used to prepare compound 11 in the process shown in Scheme VII.

The inventive process comprises providing a solution containing an oxime to be oxidized in a polar solvent containing an aqueous buffer and contacting the oxime with a molybdenum oxidation complex. A pre-formed molybdenum oxidation complex can be used, for example, the molybdenum complex of Formula II

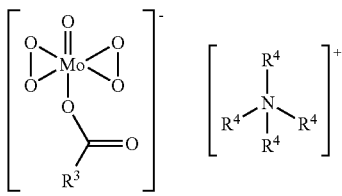

Formula II wherein R³ is a benzyl group or an aryl group, each of which is optionally substituted with alkyl substituents and R⁴ is selected from linear, branched, or cyclic alkyl of up to 12 carbon atoms. One preferred molybdenum oxidation complex is BzO⁻Mo(O₂)₂]⁻But₄N⁺, wherein R³ is benzyl. Other anionic molybdenum oxidation catalysts known are also suitable, for example, those described by Ballistreri et al., *Synlett*, 1093-4 (November 1996).

The inventors have surprisingly found that a molybdenum oxidation complex suitable for mediating oxime oxidation in the process of the present invention can be made in situ by using 1 equivalent of sodium or potassium molybdate in the presence of 1.5 equivalents 25% aqueous H₂O₂ (equivalency based on the number of moles of substrate to be oxidized).

Moreover, the inventors have found that the molybdenum oxidation complex prepared from sodium molybdate and peroxide can be used catalytically, utilizing from about 10 mole % of sodium molybdate (based on the amount of substrate to be oxidized) with from about 1.2 equivalents of peroxide to about 1.6 equivalents of peroxide based on the amount of substrate to be oxidized. It is preferred to use the minimum amount of peroxide consistent with complete oxidation of the substrate to prevent degradation of the product.

The results of the oxidation process of the present invention are sensitive to the pH of the oxidation medium. Accordingly, it is preferred to run the oxidation reaction in the presence of a buffer. Suitable buffers can be made, for example, by adding a conventional aqueous buffer made from sodium phosphonate monobasic to buffer the reaction mixture to a pH of from about pH 4.5 to about pH 8.5. The buffer is made by dissolving sodium phosphonate, monobasic salt It is preferred to use an amount of the buffer system which maintains the reaction medium at a pH of from about pH 4.5 to about pH 8.5.

Because the reaction medium utilizes an aqueous buffer it is preferred to employ polar solvents which are miscible with water. Examples of suitable solvents include acetone, acetonitrile, DMF, and NMP.

The oxidation reaction can be run at temperatures from about 0 C to about 100 C, preferably the temperature is maintained at from about 40 C to about 60 C during the oxidation reaction. In this temperature range, the substrate is completely consumed (less than about 5 mole % remains) in about 1 to about 3 hours. Longer times can be employed, however, the nitro functionalized product of the oxime oxidation of the present invention is subject to conversion to ketone under less basic reaction conditions. Accordingly long reaction times can decrease nitro-compound yield.

In a preferred embodiment, a compound of the formula:

R—CH₂—NO₂ (IB')

where R is linear, branched or cyclic alkyl, linear, branched, or cyclic alkenyl, linear, branched, or cyclic alkynl, aryl, arylalkyl, alkylaryl, hereroaryl, heterocycl, arylcycloalkyl and arylheterocycloalkyl, each of which is optionally substituted as defined in the definitions section above, is prepared in a process which comprises oxidizing an oxime of the formula:

R—HC=N—OH (IB)

where R is defined above, with sodium molybdate in hydrogen peroxide in the presence of a solvent buffered to a pH of from about 6 to about 7.5 using the NaMolyOx molybdenum oxidation complex described above.

The preparation of oxime starting materials may be made from procedures known in the art starting from, for example, the corresponding hydroxyl derivatives, compounds which in turn may be obtained commercially or by modifying known procedures. One skilled in this art would have publications such as *Chemical Abstracts* and *Beilstein* at his or her disposal and would be able to modify known synthetic routes to prepare a specific starting material.

In one embodiment, the present invention related to a process for preparing a compound according to formula I

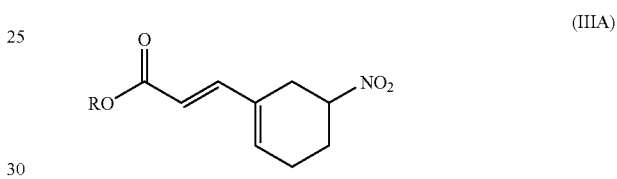

(IIIA)

wherein R is H, linear, branched or cyclic alkyl, optionally substituted, and linear branched or cyclic alkenyl, optionally substituted, wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocycloalkyl, each of which is optionally substituted from a compound of the formula:

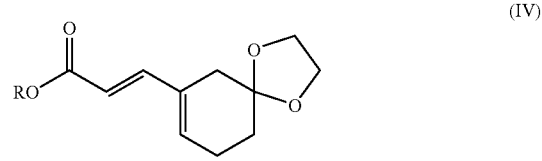

(IV)

said process comprising:

(a) removing the ketal protecting group by hydrolysis from a compound of formula II to form a compound of the formula:

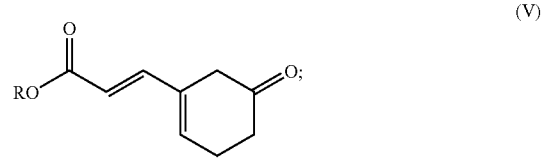

(V)

(b) converting the compound of Formula V with to an oxime of the Formula IA:

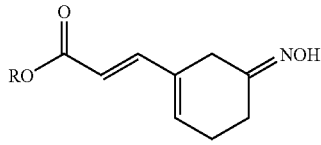

and (b) oxidizing the compound of formula (IV) with a peroxomolybdenum complex complex or sodium molybdate/hydrogen peroxide catalyst.

Preferred values for R in this process include is hydrogen, alkyl, substituted alkyl, phenyl, substituted phenyl, benzyl, or substituted benzyl, H, linear, branched or cyclic alkyl, optionally substituted, and linear branched or cyclic alkenyl, optionally substituted, wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocycloalkyl, each of which is optionally substituted. More preferred values for R in the inventive process are compounds wherein R is hydrogen, alkyl or substituted alkyl wherein the substituents are halo, phenyl, cyano, hydroxyl, alkyl, aryl, cycloalkyl, cyano, alkoxy, alkylthio, amino, —NH(alkyl), —NH(cycloalkyl), —N(alkyl)$_2$, carboxy and —C(O)O-alkyl. Especially preferred are those compounds wherein R is hydrogen or methyl.

After hydrolysis of the ketal (compound IV) is completed, the resulting ketone (compound V) can be isolated from the hydrolysis medium for conversion to the oxime at a time and/or in a place separated from the hydrolysis, or conversion to the oxime (compound IA) can be carried out in situ without isolation of the ketone. Compounds of formula IV are either known in the art or can be made by modifying known synthesis (see, e.g., U.S. Pat. No. 6,063,847, herein incorporated by reference.

The hydrolysis is performed by using an acid in a solvent at a pH of from about pH 4.5 to about pH 8.5. Preferred acids for the hydrolysis include mineral acids, such as HCl, HBr, or $H_2SO_4$, $H_3PO_4$ as well an organic acids, for example, p-toluene sulfonic acid, camphorsulfonic acid, carboxylic acids and Lewis acids, with p-toluene sulfonic acid being most preferred. Preferred solvents include polar and moderately polar solvents, for example, alcohols, nitriles, ketones, esters and ethers. Preferred solvents are acetonitrile, acetone and tetrahydrofuran ("THF"), with acetonitrile and acetone being especially preferred.

Hydrolysis can be preformed at temperatures ranging from 0° C. to the refluxing temperature of the solvent selected, preferably from about 20° C. to about 40° C.

The oxime can be prepared with or without isolation of the ketone of formula II. The oxime may be formed with conventional reagents, such as hydroxylamine and a base, for example, as described in detail in copending U.S. application Ser. No. 11/331,324, filed Jan. 12, 2006, which is incorporated herein by reference, preferably, hydroxylamine hydrochloride and pyridine. When the oxime is oxidized without isolation, it is preferred to conduct the hydrolysis of the ketal (compound IV) in mixed acetonitrile/water with p-toluene sulfonic acid. Following completion of the hydrolysis reaction, the reaction mixture is adjusted to a pH of about pH 7 by addition of an appropriate amount of aqueous sodium hydroxide and then add the hydroxylamine and pyridine directly to the hydrolysis mixture to carry out the preparation of the oxime.

If desired, after preparation of compound of formula IIIA by oxidation of the oxime of formula IA, the oxidation product can be purified by a crystallization process. In some embodiments it is preferred to crystallize the compound from an acidic solution comprising the compound, acetonitrile, and water, preferably where the solution has a pH more acidic than about pH 3, more preferably where the pH is from about pH 3 to about pH2. In some embodiments employing an acidic recrystallization solution, it is preferred to digest the crude product at ambient temperature and then cool the solution to a temperature at which it precipitates from the solution. In some embodiments it is preferred to cool to the solution to a temperature of less than about 0° C.

In some embodiments it is preferred to prepare an acidified solution of the compound of Formula IA from which the compound is crystallized by taking up the crude compound of Formula I in a neutral solution comprising acetonitrile and an aqueous sodium phosphate monobasic/sodium hydroxide buffer, heating the solution, preferably to a temperature of at least 40° C., cooling the solution to a sub-ambient temperature, preferably cooling to a temperature lower than about 10° C., and acidifying the solution, preferably to a pH of at least about pH 3, more preferably to a pH of from about pH 3 to about pH 2. Preferably when this procedure is followed, after acidification the solution temperature is reduced to a temperature of about 5° C. or lower.

In some embodiments, following the crystallization procedures it is preferred to collect the precipitate by vacuum filtration, wash the filter cake with cold water and dry the washed filter cake in an air draft oven at an oven temperature of about 45° C.

The following non-limiting examples are provided to illustrate further the present invention. It will be apparent to those skilled in the art that many modifications, variations and alterations to the present disclosure, both to materials, methods and reaction conditions, may be practiced. All such modifications, variations and alterations are intended to be within the spirit and scope of the present invention.

EXAMPLES

Unless otherwise stated, the following abbreviations in the Examples below:
ml=milliliters
g=grams
m.p.=melting point
DMSO-$d_6$=dimethyl-$d_6$ sulfoxide All NMR data is collected on 400 MHz NMR spectrometers unless otherwise indicated.

Preparation of 3-(5-oximecyclohex-1-enyl) acrylic acid (2)

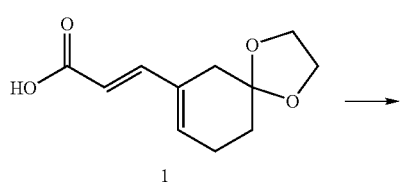

1

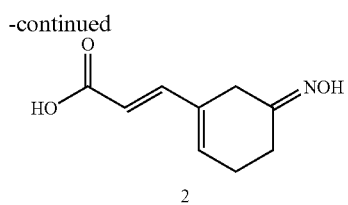

To a 3 three-neck flask equipped with an agitator, thermometer and a nitrogen inlet, 660 mL of water, 99 g (0.52 moles) of p-toluenesulfonic acid monohydrate and 110 g (0.52 mols) of 1 were added. The reaction mixture was agitated at 20° C. for 20 hours and was then cooled to 0° C. The pH was adjusted to 6.5 by adding sodium hydroxides aqueous solution. 40 g (0.58 mol) of hydroxylamine hydrochloride dissolved in 220 mL of water was slowly added to the reaction mixture while maintaining the temperature at 0° C. Compound 2 precipitated as crystalline white solid; yield: 74 g (77%). m.p. 204.5 $^1$H-NMR (DMSO-$d_6$) δ12.2(brs, 1H), 10.5 (s, 1H), 7.31 (d, J=15.8 Hz, 1H), 6.38 (s, 1H), 5.71 (d, J=15.7, 1H), 3.09 (s, 2H), 2.36 (s 2H), 2.34 (d, J=5.31, 2H).

Preparation of 3-(5-nitrocyclohex-1-enyl) acrylic acid (6)

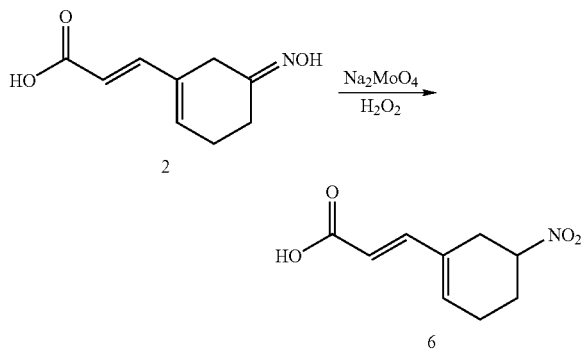

To a 3 three-neck flask equipped with an agitator, thermometer and a nitrogen inlet, was added 730 mL of water and 100 g (0.72 mol) of sodium phosphate monobasic monohydrate. The pH of the reaction mixture was adjusted to 6.4 by the addition of 25% sodium hydroxide aqueous solution. 73 g of (2) (0.40 mol), 97.8 g of sodium molybdate dihydrate (0.40 mol) and 730 mL of $CH_3CN$ were added to the reaction mixture. The resulting mixture was heated to 50° C. followed by slowly adding 62 mL of 30% hydrogen peroxide aqueous solution while maintaining the temperature at 50 ° C. The reaction mixture was agitated at 50° C. for 1 to 2 hours and then cooled to 20° C. Next a solution of 10.22 g of sodium sulfite in 73 mL of water was added to the reaction mixture. The reaction mixture was then agitated for 30 minutes at 20° C. and concentrated under vacuum. To the reaction mixture was added 365 mL water, and the reaction mixture was cooled to 5° C. and the pH was adjusted to 2-3 by the addition of 37% hydrochloric acid aqueous solution. Compound 6 precipitated out and was then filtered, washed and dried to provide 55 g of a light brown colored solid; yield 69%, m.p. 162.8° C. $^1$H-NMR (DMSO-$d_6$) δ 12.2 (s, 1H), 7.22 (d, J=15.8 Hz, 1H), 6.28 (s, 1H), 5.78 (d, J=15.8 Hz,1H), 4.97 (s,1H), 2.74 (m, 2H), 2.33 (brs 2H), 2.08-2.22 (m, 2H).

Purification of 3-(5-nitrocyclohex-1-enyl) acrylic acid (Compound 6)

The compound 6 prepared in accordance with Example 1 was purified by one of two purification procedures.

Procedure 1

Into a 2 L three neck flask equipped with an agitator, thermometer, and a nitrogen inlet, was added 50.0 g of Compound 6 prepared above, 500 mL of water and 350 mL of acetonitrile. The pH of the solution was adjusted to 2.5 with 5% hydrochloric acid aqueous solution at 20° C. The suspension was stirred at 20° C. for 1 hour, then cooled to 0° C., stirred for one additional hour at 0° C. and collected via filtration. The collected compound 6 was washed with cold water and dried in an air-draft oven set at a temperature of 45° C. to provide 44.1 g of Compound 6 as off-white solid (88.2% w/w yield, purity 97.0% w/w). The purified compound 6 was characterized by m.p. 162.8° C. (DSC onset point) and $^1$H-NMR (DMSO-$d_6$) ☐ 12.2 (s, 1H), 7.22 (d, J=15.8 Hz, 1H), 6.28 (s, 1H), 5.78 (d, J=15.8 Hz, 1H), 4.97 (s, 1H), 2.74 (m, 2H), 2.33 (brs, 2H), 2.08-2.22 (m, 2H).

Procedure 2

Into a 2 L three neck flask equipped with an agitator, thermometer, and a nitrogen inlet, was added 69 g of sodium phosphate monobasic monohydrate and 500 mL of water. An aqueous 25% sodium hydroxide solution (27.5 mL) was added to adjust pH to 6.5. To above solution was added 50.0 g of Compound 6 and 350 mL of acetonitrile. The pH was adjusted to 7.0 with additional 25% sodium hydroxide aqueous solution. The mixture was heated to 40° C. and stirred for 15 minutes. At the end of 15 minutes the mixture was cooled to a temperature of less than 10° C. To the cooled solution was added 60 mL of 37% hydrochloric acid aqueous solution to adjust solution pH to pH 2 to pH 3. Purified compound 6 began to precipitate from the solution forming a suspension. The suspension was cooled to a temperature of less than 5° C. and stirred for one additional hour while maintaining the suspension at a temperature below 5° C. At the end of one hour the solid compound 6 was collected via filtration. The collected compound 6 was washed with cold water and dried in an air-draft oven set at a temperature of 45 to provide 44.7 g of Compound 6 as off-white solid (89.4% w/w yield, purity 98.1% w/w). The purified compound 6 thus obtained was characterized by. m.p. 162.8° C. (DSC onset point) and $^1$H-NMR (DMSO-$d_6$) ☐ 12.2 (s, 1H), 7.22 (d, J =15.8 Hz, 1H), 6.28 (s, 1H), 5.78 (d, J =15.8 Hz, 1H), 4.97 (s, 1H), 2.74 (m, 2H), 2.33 (brs, 2H), 2.08-2.22 (m, 2H).

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A process for preparing a compound of the formula:

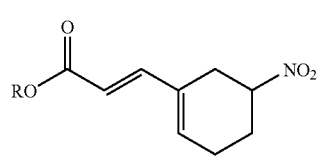

wherein R is H, linear, branched or cyclic alkyl, optionally substituted, and linear branched or cyclic alkenyl, optionally substituted, wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocycloalkyl, each of which is optionally substituted wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocycloalkyl, halo, phenyl, cyano, hydroxyl, alkyl, aryl, cycloalkyl, cyano, alkoxy, alkylthio, amino, —NH(alkyl), —NH(cycloalkyl), —N(alkyl)$_2$, carboxy and —C(O)O-alkyl,
from a compound of the formula:

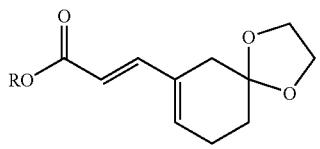

(II)

said process comprising:
a) removing the ketal protecting group by hydrolysis from a compound of formula II to form a compound of the formula:

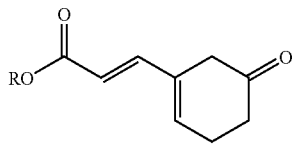

(III)

followed by coverting a compound of formula III, with or without, isolation to an oxime of the formula:

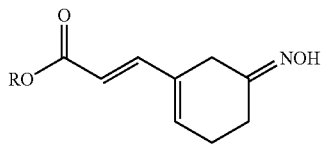

(IV)

and
b) oxidizing the compound of formula (IV) with a peroxomolybdenum complex complex or sodium molybdate/hydrogen peroxide catalyst.

2. The process according to claim 1, wherein R is hydrogen, alkyl, substituted alkyl, phenyl, substituted phenyl, benzyl, or substituted benzyl.

3. The process according to claim 1, wherein R is hydrogen, alkyl or substituted alkyl wherein the substituents are halo, phenyl, cyano, hydroxyl, amino.

4. The process according to claim 3 wherein R is hydrogen, methyl, a lower alkyl, benzyl, or substituted benzyl.

5. The process according to claim 1 wherein the hydrolysis is performed by using an acid in a solvent at a pH of from about pH 4.5 to about pH 8.5.

6. The process according to claim 5, wherein the acid is p-toluene sulfonic acid, a mineral acid, or SAC and the solvent is acetonitrile, acetone or tetrahydrofuran.

7. The process according to claim 6, wherein the acid is p-toluene sulfonic acid and the solvent is tetrahydrofuran or acetonitrile.

8. The process according to claim 1, wherein hydroxylamine hydrochloride in base is used to covert the ketone to the oxime of formula.

9. The process according to claim 1 wherein the conversion occurs without isolating the ketone.

10. The process according to claim 1, wherein the catalyst is a peroxomolybdenum complex.

11. The process according to claim 1, wherein the peroxomolybdenum complex is $[BzO^-Mo(O_2)_2]^-Bu'_4N^+$.

12. The process according to claim 1, wherein the catalyst is sodium molybdate/hydrogen peroxide.

13. The process according to claim 7, wherein the catalyst for the oxidation is sodium molybdate/hydrogen peroxide and the solvent for the oxidation is acetonitrile.

14. A compound of the formula:

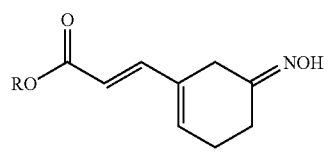

(IV)

wherein R is H, optionally substituted alkyl, optionally substituted alkenyl, optionally substituted alkynyl, optionally substituted cycloalkyl, optionally substituted cycloalkenyl, optionally substituted aryl, optionally substituted arylalkyl, optionally substituted alkylaryl, optionally substituted heteroaryl, optionally substituted heterocycle, optionally substituted heterocycloalkenyl, optionally substituted arylcycloalkyl, or optionally substituted arylheterocycloalkyl.

15. The compound according to claim 14, wherein R is H, optionally substituted alkyl or optionally substituted phenyl.

16. The compound according to claim 14, wherein R is H or methyl.

17. A process for the formation of a nitro-containing compound form an oxime comprising oxidizing an oxime with sodium molybdate and hydrogen peroxide.

18. The process of claim 17 wherein the oxime compound contains also at least one moiety selected from a carbon-carbon double bond and an oxidation sensitive functional group.

19. The process of claim 17 wherein the sodium molybdate is present in a catalytic amount.

20. The process claim 18 wherein the sodium molybdate is present in a catalytic amount.

21. A process for the introduction of nitro-group functionality into a compound which contains also a site of unsaturation and/or oxygen functionality by direct (one step) oxidation of an oxime functional group mediated by a molybdenum VI/VII peroxo complex, the process comprising:

(a) providing a substrate of Formula I containing an oxime functional group;

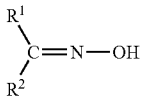

Formula I wherein $R^1$ and $R^2$ are selected independently from linear, branched or cyclic alkyl and linear, branched or cyclic alkenyl groups, optionally substituted with carboxylic, ester, halo, phenyl, cyano, alkyl, alkenyl aryl, cycloalkyl, cyano, alkoxy, alkylthio, —N(alkyl)$_2$, —N(cycloatkyl)$_2$, -carboxy and —C(O)O-alkyl functionality, or $R^1$ and $R^2$ are taken together to form a cycloalkenyl substitutent which is optionally substituted with one or more groups selected from linear, branched or cyclic alkyl and linear, branched or cyclic alkenyl functional groups, each of which may optionally be substituted with alkenyl. -carboxy, ester, halo, phenyl, cyano, alkyl, aryl, cycloalkyl, cyano, alkoxy, alkylthio, —N(alkyl)$_2$, and —N(cycloalkyl)$_2$, functional groups, with the proviso that at least one of $R^1$ or $R^2$ contains a carbon/carbon double bond; and (b) contacting said substrate of Formula I with a molybdenum oxidation complex comprising a mixture of hydrogen peroxide and molybdate salt selected from sodium molybdate, and potassium molybdate, thereby oxidizing said oxime functional group to a nitro functional group to yield the structure of Formula III.

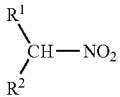

Formula III wherein $R^1$ and $R^2$ are as defined above.

22. A process for the introduction of nitro-group functionality into a compound which contains also a site of unsaturation and/or oxygen functionality by direct (one step) oxidation of an oxime functional group mediated by a molybdenum VI/VII peroxo complex, the process comprising:

(a) providing a substrate of Formula I containing an oxime functional group;

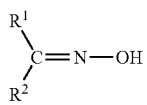

Formula I wherein $R^1$ and $R^2$ are selected independently from linear, branched or cyclic alkyl and linear, branched or cyclic alkenyl groups, optionally substituted with carboxylic, ester, halo, phenyl, cyano, alkyl, alkenyl aryl, cycloalkyl, cyano, alkoxy, alkylthio, —N(alkyl)$_2$, —N(cycloalkyl)$_2$, -carboxy and —C(O)O-alkyl functionality, or $R^1$ and $R^2$ are taken together to form a cycloalkenyl substitutent which is optionally substituted with one or more groups selected from linear, branched or cyclic alkyl and linear, branched or cyclic alkenyl functional groups, each of which may ontionally be substituted with alkenyl, -carboxy, ester, halo, phenyl, cyano, alkyl, aryl, cycloalkyl, cyano, alkoxy. alkylthio, —N(alkyl)$_2$, and —N(cycloalkyl)$_2$,functional groups, with the proviso that at least one of $R^1$ or $R^2$ contains a carbon/carbon double bond; and (b) contacting said substrate of Formula I with a molybdenum oxidation complex comprising an anionic molybdenum peroxide complex, thereby oxidizing said oxime functional group to a nitro functional group to yield the structure of Formula III,

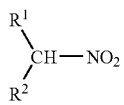

Formula III wherein $R^1$ and $R^2$ are as defined above.

* * * * *